United States Patent [19]
Jona et al.

[11] Patent Number: 5,891,461
[45] Date of Patent: Apr. 6, 1999

[54] TRANSDERMAL ADMINISTRATION OF OLANZAPINE

[75] Inventors: Janan Jona, Sunnyvale; Priti Joshi, San Jose; Asha Ramdas, Mountain View, all of Calif.

[73] Assignee: Cygnus, Inc., Redwood City, Calif.

[21] Appl. No.: 528,106

[22] Filed: Sep. 14, 1995

[51] Int. Cl.⁶ .................................................. A61F 13/00
[52] U.S. Cl. .......................................... 424/449; 424/448
[58] Field of Search .................... 424/441, 449, 424/448

[56] References Cited

U.S. PATENT DOCUMENTS

| | | | |
|---|---|---|---|
| 4,220,152 | 9/1980 | Dresback | 424/439 |
| 4,379,454 | 4/1983 | Campbell et al. | 424/448 |
| 4,412,036 | 10/1983 | Pedersen et al. | 525/54.26 |
| 4,438,258 | 3/1984 | Graham | 528/361 |
| 4,467,012 | 8/1984 | Pedersen et al. | 442/118 |
| 4,644,033 | 2/1987 | Gnanou et al. | 524/540 |
| 4,698,062 | 10/1987 | Gale et al. | 424/449 |
| 4,731,391 | 3/1988 | Garvey | 521/137 |
| 4,849,224 | 7/1989 | Chang et al. | 424/434 |
| 4,915,950 | 4/1990 | Miranda et al. | 424/448 |
| 4,985,467 | 1/1991 | Kelly et al. | 521/52 |
| 5,000,955 | 3/1991 | Gould et al. | 424/497 |
| 5,120,546 | 6/1992 | Hansen et al. | 424/449 |
| 5,160,328 | 11/1992 | Cartmell et al. | 604/307 |
| 5,203,768 | 4/1993 | Haak et al. | 604/20 |
| 5,216,098 | 6/1993 | Almed et al. | 526/288 |
| 5,225,198 | 7/1993 | Sharma | 424/443 |
| 5,229,382 | 7/1993 | Chakrabarti et al. | 514/220 |
| 5,352,508 | 10/1994 | Cheong | 424/443 |
| 5,423,737 | 6/1995 | Cartmell et al. | 602/57 |
| 5,457,101 | 10/1995 | Greenwood et al. | 514/220 |
| 5,464,628 | 11/1995 | Jalonen | 424/448 |
| 5,503,843 | 4/1996 | Santus et al. | 424/448 |
| 5,605,897 | 2/1997 | Beasley, Jr. | 514/220 |

FOREIGN PATENT DOCUMENTS

| | | |
|---|---|---|
| 0 454 436 A1 | 10/1991 | European Pat. Off. . |
| 0 528 091 A1 | 2/1993 | European Pat. Off. . |
| 0 582 368 A1 | 2/1994 | European Pat. Off. . |
| 91/05809 | 5/1991 | WIPO . |
| 92/20324 | 11/1992 | WIPO . |
| 97/09971 | 3/1997 | WIPO . |
| 97/24148 | 7/1997 | WIPO . |

OTHER PUBLICATIONS

Chen et al. (1985), "Synthetic and natural polymers," *Absorbency* Ch. VI:197–216.

Fuller et al., "Neuroendocrine Evidence for Antagonism of Serotonin and Dopamine Receptors by Olanzapine (LY170053), an Antipsychotic Drug Candidate," *Research Communications in Chemical Pathology and Pharmacology* 77(1):87–93 (1992).

Moore et al., "The Behavioral Pharmacology of Olanzapine, a Novel 'Atypical' Antipsychotic Agent," *Journal of Pharmacology and Experimental Therapeutics* 262(2):545–551 (1992).

Tran et al., "Clinical Efficacy and Safety of Olanzapine, A New Atypical Antipsychotic Agent," *Neuropsychopharmacology* 10(3S), Part 2 (1994).

*Primary Examiner*—D. Gabrielle Phelan
*Attorney, Agent, or Firm*—Dianne E. Reed; Bozicevic & Reed LLP

[57] ABSTRACT

Transdermal administration of olanzapine and pharmaceutically acceptable acid addition salts thereof is described. The method involves treating an individual suffering from or susceptible to psychosis, acute mania or mild anxiety states, particularly those afflicted with schizophrenia or schizophreniform illnesses, by administering olanzapine or a salt thereof through the skin or mucosal tissue, for a time period and at an administration rate effective to alleviate the symptoms of the disease. Pharmaceutical formulations and drug delivery systems for administering olanzapine are provided as well.

23 Claims, 11 Drawing Sheets

TRANSDERMAL ADMINISTRATION OF OLANZAPINE

TECHNICAL FIELD

This invention relates generally to transdermal drug delivery, and more particularly relates to methods and drug delivery systems for administering olanzapine transdermally. The invention additionally relates to pharmaceutical compositions formulated for transdermal administration of olanzapine.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastro-intestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration.

Relatively recent advances in transdermal drug delivery have enabled effective administration of a variety of drugs through the skin. These advances include the development of a number of skin penetration enhancing agents, or "permeation enhancers," to increase skin permeability, as well as non-chemical modes for facilitating transdermal delivery, e.g., the use of iontophoresis, electroporation or ultrasound. Nevertheless, the number of drugs that can be safely and effectively administered through the skin, without concomitant problems such as irritation or sensitization, remains limited.

The present invention is directed to the transdermal administration of 2-methyl-10-(4-methyl-1-piperazinyl)-4H-thieno[2,3-b][1,5]benzodiazepine, also known as "olanzapine." The drug is described in U.S. Pat. No. 5,229,382 to Chakrabarti et al., issued Jul. 20, 1993, and assigned to Lilly Industries Limited. Reference may be had thereto for any information concerning methods for synthesizing or using olanzapine not explicitly included herein.

Olanzapine

Olanzapine is a novel antagonist of dopamine at the D-1 and D-2 receptors, and in addition has antimuscarinic anticholinergic properties and antagonist activity at 5HT-2 receptor sites and at noradrenergic α-receptors (Moore et al., *J. Pharmacol. Exp. Ther.* 262(2):545–551 (1992)). The drug has relaxant, anxiolytic and anti-emetic properties, and, as explained in the Chakrabarti et al. patent referenced above, is useful in the treatment of psychosis, acute mania and mild anxiety states, and is particularly useful in the treatment of schizophrenia and schizophreniform illnesses.

Earlier methods for treating schizophrenia typically involved the use of the antipsychotic agents haloperidol, clozapine and flumezapine (7-fluoro-2-methyl-10-(4-methyl-1-piperazinyl)-4H-thieno[2,3-b][1,5]benzodiazepine). However, as explained in U.S. Pat. No. 5,229,382 to Chakrabarti et al., these drugs were problematic in a number of ways. Haloperidol was found to cause a high incidence of extra pyramidal symptoms, e.g., Parkinsonism, acute dystonic reactions, akathisia, tardive dyskinesia and tardive dystonia. While clozapine was claimed to be substantially free of such extra pyramidal symptoms, it was found to cause agranulocytosis in some patients, a condition resulting in a lowered white blood cell count to a potentially life-threatening degree. Flumazepine was found to result in still additional problems, leading to termination of clinical trials before commercialization, the problems primarily related to an unacceptably high levels of certain enzymes, e.g., creatinine phosphokinase, serum glutamate oxalacetic transaminase and serum glutamate pyruvate transaminase. A related drug, chlorpromazine, has also been found to give rise to a number of problems.

Olanzapine has been developed as a drug which is highly effective in the treatment of psychosis, acute mania and mild anxiety states. Olanzapine has been found to be a very safe and effective antipsychotic agent which does not appear to give rise to extra pyramidal symptoms, agranulocytosis, or unacceptably high enzyme levels. Olanzapine has been established to be more potent than clozapine in blocking 5HT2 and dopamine-D2 in studies in rodents (Fuller et al., *Research Communications in Chemical and Pathology and Pharmacology* 77:1187–1193 (1992)). Additionally, in Phase II, double-blind, randomized, placebo controlled clinical trials, it was concluded that olanzapine is effective in treating both the positive and negative symptoms of schizophrenia and is well-tolerated (P.V. Tran et al., *Neuropsychopharmacology* 10(3):267S, suppl., pt. 2 (1994)).

Currently, olanzapine is administered orally or by injection. While, as alluded to above, the drug is an extremely effective antipsychotic agent, drug non-compliance is a serious problem, and is believed to account for approximately one-third of all short-stay hospital costs. Transdermal administration of olanzapine, as disclosed and claimed herein, significantly enhances patient compliance by providing an advanced delivery system useful for administering the drug over an approximately three- to seven-day period.

There are a number of other advantages to administering olanzapine transdermally as well: gastrointestinal and other side effects associated with oral administration are substantially avoided; continuous delivery provides for sustained blood levels; the transdermal patch is easily removable if any side effects do occur; and the likelihood of patient acceptance is significantly improved. In general, steady-state, transdermal delivery of the drug seems to provide a far better side effect profile overall than is associated with oral administration.

None of the art of which applicants are aware describes a transdermal drug delivery system for administering olanzapine. Nor does the art set forth data on skin permeability or therapeutic administration rates with respect to such compounds. To the best of applicants' knowledge, then, the transdermal administration of olanzapine is unknown and completely unsuggested by the art.

SUMMARY OF THE INVENTION

Accordingly, it is a primary object of the present invention to address the above-mentioned need in the art by providing methods, pharmaceutical formulations and systems for the transdermal administration of olanzapine or a pharmaceutically acceptable acid addition salt thereof.

It is another object of the invention to provide a method for treating psychosis, acute mania or mild anxiety states, particularly schizophrenia or schizophreniform illnesses, by administering olanzapine or a pharmaceutically acceptable acid addition salt thereof through a predetermined area of intact skin or mucosal tissue for a time period and at an administration rate effective to alleviate the symptoms at issue.

It is still another object of the invention to provide such a method which involves the transdermal administration of a pharmaceutically acceptable acid addition salt of olanzapine.

It is a further object of the invention to provide such a method in which olanzapine or a pharmaceutically acceptable acid addition salt thereof is administered in conjunction with a skin permeation enhancer.

It is a further object of the invention to provide olanzapine-containing compositions formulated for transdermal delivery.

It is still a further object of the invention to provide a "solid matrix" type transdermal system for administering olanzapine as provided herein which comprises a laminated composite of a backing layer and a contact adhesive layer which contains the drug and serves as the basal surface which contacts the skin or mucosal tissue during use.

It is yet a further object of the invention to provide a transdermal system for administering olanzapine as provided herein which comprises a laminated composite of a backing layer, a contact adhesive layer which serves as the basal surface and contacts the skin or mucosal tissue during use, and, incorporated therebetween, a polymeric matrix which contains the drug and serves as the drug reservoir.

It is still a further object of the invention to provide a transdermal system for administering olanzapine as provided herein, in the form of a patch having an internal reservoir of a liquid, gel or foam with the drug dispersed or adsorbed therein.

Still further objects of the invention are to provide transdermal systems for administering olanzapine, containing high capacity polyurethane hydrogel drug reservoirs or reservoirs of superabsorbent material as will be described elsewhere herein.

Additional objects, advantages and novel features of the invention will be set forth in part in the description which follows, and in part will become apparent to those skilled in the art upon examination of the following, or may be learned by practice of the invention.

In one aspect of the invention, a method is provided for treating an individual suffering from or susceptible to psychosis, acute mania or mild anxiety states, particularly schizophrenia and schizophreniform illnesses, by transdermally administering a therapeutically effective amount of olanzapine or a pharmaceutically acceptable acid addition salt thereof, for a time period and at an administration rate effective to alleviate the symptoms at issue. The method is premised on the discovery that olanzapine and pharmaceutically acceptable salts thereof may be administered through the skin or mucosal tissue to achieve desired systemic effects. In a preferred embodiment, a skin permeation enhancer is coadministered with the drug so as to increase permeability thereto and achieve more rapid delivery.

It should be noted that while the present invention is directed to the treatment of individuals suffering from or susceptible to psychosis, acute mania or mild anxiety states, and is particularly useful in the treatment of schizophrenia or schizophreniform illnesses, the present method may extend to any use of olanzapine deriving from its activity an antagonist of dopamine at the D-1 and D-2 receptors, its antimuscarinic anti-cholinergic properties, and/or its antagonist activity at 5HT-2 receptor cites and noradrenergic α-receptors.

In another aspect of the invention, a therapeutic system for transdermal administration of olanzapine is provided. The system is a laminated composite comprising a backing layer, a drug reservoir, and a means for affixing the composite to the skin. The drug reservoir and the affixing means may be distinct, such that a separate contact adhesive layer is provided which serves as the basal surface of the device, or the drug reservoir may itself be comprised of an adhesive layer which is suitable for contacting and adhering to the skin. Such therapeutic systems are in the nature of "solid matrix" type transdermal patches. Alternative systems, containing the drug in a liquid, gel or foam reservoir, may, however, be used as well. The transdermal system is preferably constructed such that an effective dose of olanzapine or a pharmaceutically acceptable acid addition salt thereof will be delivered for a period in the range of about three to seven days.

DETAILED DESCRIPTION OF THE INVENTION

Before describing the present invention in detail, it is to be understood that this invention is not limited to particular formulations or transdermal systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "an excipient" or "a vehicle" includes mixtures of excipients or vehicles, reference to "an adhesive layer" includes reference to two or more such layers, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream.

By "therapeutically effective" amount is meant a nontoxic but sufficient amount of a compound to provide the desired therapeutic effect, in the present case, that dose of olanzapine which will be effective in relieving or preventing symptoms of psychosis, acute mania, mild anxiety, or the like. An "effective" amount of a permeation enhancer as used herein means an amount that will provide the desired increase in skin permeability and, correspondingly, the desired depth of penetration, rate of administration, and amount of drug delivered.

By "predetermined area of skin" is intended a defined area of intact unbroken living skin or mucosal tissue. That area will usually be in the range of about 1 cm$^2$ to about 100 cm$^2$, more usually in the range of about 20 cm$^2$ to about 60 cm$^2$. However, it will be appreciated by those skilled in the art of transdermal drug delivery that the area of skin or mucosal tissue through which drug is administered may vary significantly, depending on patch configuration, dose, and the like.

When transdermal administration of "olanzapine" per se is indicated herein, it is to be understood that the described method, formulation or system extends to pharmaceutically acceptable acid addition salts as well.

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus as described in the Examples herein.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" as used herein may also refer to stabilizers, crystallization inhibitors, or other types of additives useful for facilitating transdermal drug delivery.

The present method of transdermally delivering olanzapine may vary, but necessarily involves application of a composition containing olanzapine or a pharmaceutically acceptable acid addition salt thereof to a predetermined area of the skin or mucosal tissue for a period of time sufficient to provide an effective blood level of drug for a desired period of time. The method may involve direct application of the composition as an ointment, gel, cream, or the like, or may involve use of a drug delivery device as taught in the art, e.g., in commonly assigned U.S. Pat. Nos. 4,915,950, 4,906,463, 5,091,186 or 5,246,705, or as described below.

As noted above, olanzapine may be administered as the base or in the form of a pharmaceutically acceptable acid addition salt. As will be appreciated by those skilled in the art, the base form of the drug can be converted to an acid addition salt by treatment with a stoichiometric excess of a selected acid. Such acid addition salts may be formed, for example, with inorganic acids such as hydrochloric acid, hydrobromic acid, sulfuric acid, nitric acid, phosphoric acid, and the like, or with organic acids such as acetic acid, propionic acid, glycolic acid, pyruvic acid, oxalic acid, malic acid, malonic acid, succinic acid, maleic acid, hydroxymaleic acid, fumaric acid, tartaric acid, citric acid, benzoic acid, cinnamic acid, mandelic acid, methanesulfonic acid, ethanesulfonic acid, p-toluenesulfonic acid, naphthalene-2-sulfonic acid, salicylic acid and the like.

It will generally be necessary to administer olanzapine or an acid addition salt thereof in conjunction with a permeation enhancer. Suitable enhancers include, but are not limited to, dimethylsulfoxide (DMSO), dimethyl formamide (DMF), N,N-dimethylacetamide (DMA), decylmethylsulfoxide ($C_{10}$MSO), polyethylene glycol monolaurate (PEGML), propylene glycol (PG), propylene glycol monolaurate (PGML), glycerol monolaurate (GML), methyl laurate (ML), lauryl lactate (LL), isopropyl myristate (IPM), terpenes such as menthone, $C_2$–$C_6$ alkanediols, particularly 1,2-butanediol, lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. Vegetable oil permeation enhancers, as described in commonly assigned U.S. Pat. No. 5,229,130 to Sharma, may also be used. Such oils include, for example, safflower oil, cotton seed oil and corn oil.

One group of preferred enhancers for use in conjunction with the transdermal administration of olanzapine and acid addition salts thereof are esters given by the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups. In the preferred embodiment herein, the ester component is a lower alkyl ($C_1$–$C_3$) laurate (i.e., m is 10 and n is 1), and in a particularly preferred case is "PGML." It will be appreciated by those skilled in the art that the commercially available material sold as "PGML" is typically a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially.

Also preferred are fatty acids and fatty alcohols corresponding to the above-defined fatty esters. Thus, fatty acids useful as permeation enhancers herein will generally have the formula $CH_3(CH_2)_mCOOH$, where m is as above, while the fatty alcohols will have the formula $CH_3(CH_2)_mCH_2OH$ Other preferred enhancer compositions are wherein a fatty ester as described above is combined with an ether component selected from the group consisting of diethylene glycol monoethyl ether and diethylene glycol monomethylether. Such enhancer compositions are described in detail in U.S. Pat. Nos. 5,053,227 and 5,059,426 to Chiang et al., both of common assignment herewith.

Particularly preferred permeation enhancers are selected from the group consisting of $C_2$–$C_6$ alkanediols, fatty esters having the structural formula $[CH_3(CH_2)_mCOO]_nR$, fatty acids having the structural formula $CH_3(CH_2)_mCOOH$, fatty alcohols having the structural formula $CH_3(CH_2)_mCH_2OH$, and mixtures thereof.

The amount of enhancer present in the composition will similarly depend on a number of factors, e.g., the strength of the particular enhancer, the desired increase in skin permeability, rate of administration, and amount of drug delivered.

The drug reservoir used in a transdermal system for administering olanzapine will generally comprise on the order of 20 wt. % to 80 wt. % reservoir material (e.g., adhesive polymer, hydrogel, or the like), with the remainder of the reservoir comprised of drug formulation, i.e., olanzapine, enhancer, and any carriers or vehicles which may be used. Typically, although not necessarily, the drug formulation will contain on the order of 1 wt. % to 20 wt. % olanzapine and, correspondingly, 80 wt. % to 99 wt. % enhancer and other vehicles. In this way, the composition may be optimized to produce a transdermal system capable of delivering olanzapine over an approximately three- to seven-day period (with patches worn for longer periods generally corresponding to lower dose systems).

Figure 1:
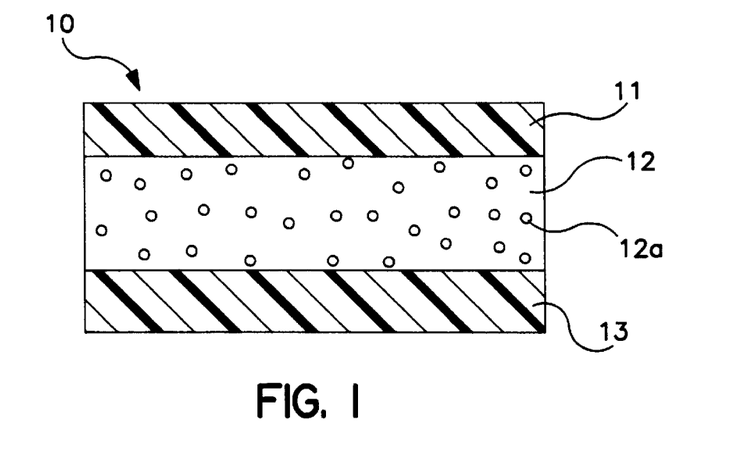
FIG. 1 illustrates in schematic form one embodiment of a solid matrix-type transdermal delivery system which may be used in conjunction with the present invention.

One type of transdermal system for transdermally administering an indolone compound of Formula (I) is "solid matrix" type system shown in FIG. 1. The composite, generally designated 10, comprises a backing layer 11, a reservoir layer 12 containing drug 12a either dispersed therein, or adsorbed or absorbed by a particulate hydrophilic material, and a release liner 13.

The backing layer 11 functions as the primary structural element of the device and provides the device with much of its flexibility, drape and, preferably, occlusivity. The material used for the backing layer should be inert and incapable of absorbing drug, enhancer or other components of the pharmaceutical composition contained within the device. The backing is preferably made of one or more sheets or films of a flexible elastomeric material that serves as a protective covering to prevent loss of drug and/or vehicle via transmission through the upper surface of the device, and will preferably impart a degree of occlusivity to the device, such that the area of the skin covered on application becomes hydrated. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

The reservoir layer 12 in FIG. 1 doubles as the means for containing drug and as an adhesive for securing the device to the skin during use. That is, as release liner 13 is removed prior to application of the device to the skin, reservoir layer 12 serves as the basal surface of the device which adheres to the skin. Reservoir layer 12 is comprised of a pressure-sensitive adhesive suitable for long-term skin contact. It must also be physically and chemically compatible with olanzapine or the acid addition salt thereof, and the carriers and vehicles employed. The reservoir layer will generally range in thickness from about 1 to about 100 microns, preferably in the range of approximately 20 to 75 microns. Suitable materials for this layer include, for example, polysiloxanes, polyisobutylenes, polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred adhesive materials for use as reservoir layer 12 are acrylates, silicones and polyurethanes.

Release liner 13 is a disposable element which serves to protect the device prior to application. Typically, the release liner is formed from a material impermeable to the drug, vehicle and adhesive, and which is easily stripped from the contact adhesive. Release liners are typically treated with silicone or fluorocarbons. Silicone-coated polyester is presently preferred.

In a variation on this embodiment, reservoir layer 12 comprises a matrix of a continuous hydrophobic polymer phase, with a particulate phase of a hydrated inorganic silicate and drug adsorbed or absorbed thereby. Such a system is described, for example, in co-pending, commonly assigned U.S. Patent application Ser. No. 08/056,076, filed Apr. 30, 1993, and entitled "Two-Phase Matrix for Sustained Release Drug Delivery Device" (published internationally as WO94/07468 on Apr. 14, 1994). As explained in that application, polymers which may be used as the continuous hydrophobic phase are polysiloxanes, polyisobutylene, solvent-based hydrophobic polyacrylates, polyurethanes, plasticized ethylene-vinyl acetate copolymers, low molecular weight polyether block amide copolymers, styrene-butadiene polymers, and vinyl acetate-based adhesives, with the hydrophobic polymer normally constituting about 30 wt. % to 95 wt. %, more typically 40 wt. % to 60 wt. %, of the matrix. The dispersed inorganic silicate is in the form of particulates that are typically in the non-colloidal size range of 0.001 to 0.1 mm, more usually 0.01 to 0.05 mm.

Preferably, the matrix in this embodiment additionally contains a dispersing agent which aids in maintaining the particulate phase dispersed in the continuous phase. Anionic, cationic, amphoteric or nonionic dispersing agents may be used. Preferably, the dispersing agent is a non-ionic surfactant such as a polyethylene-polyoxypropylene glycol copolymer (e.g., that sold under the "Pluronic" trademark) or a polyoxyethylene sorbitan ester (e.g., that sold under the "Tween" trademark); the dispersing agent will normally constitute about 0.5 wt. % to 10 wt. % of the matrix, more usually 3 wt. % to 6 wt. % of the matrix.

These matrices are prepared by dissolving the drug in water (with, optionally, additional hydrophilic polar solvents) and contacting the hydrophilic particulate material with the resulting solution to permit the aqueous solution to be absorbed by the particulate material. The mixture will typically have the texture of a paste. The hydrophobic components of the matrix and the dispersing agent, preferably in admixture, are added to the paste with vigorous mixing to form a viscous dispersion. This dispersion may be formed into appropriate shapes and excess solvent removed therefrom.

Figure 2:
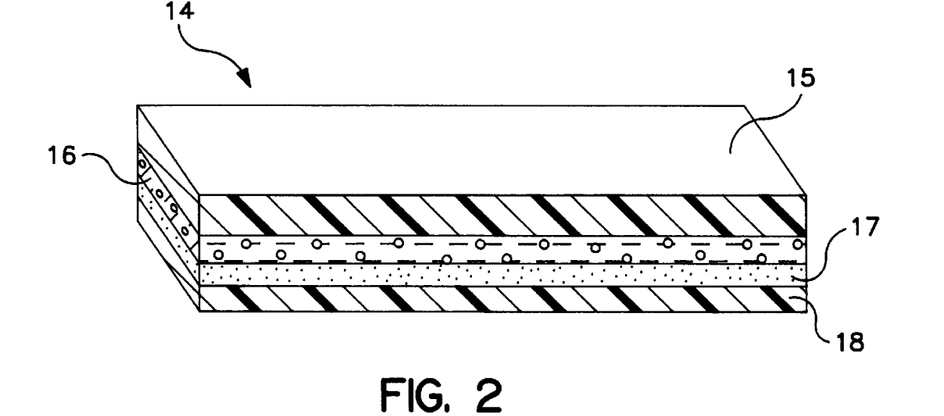
FIG. 2 illustrates in schematic form an alternative embodiment of a solid matrix-type transdermal delivery system which may be used in conjunction with the present invention.

FIG. 2 illustrates a different type of laminated composite that may serve as the transdermal delivery system herein. That system is shown generally at 14, with backing layer 15, drug reservoir 16, contact adhesive layer 17, and release liner 18. The backing layer and release liner are as described above with respect to the structure of FIG. 1. With regard to drug reservoir 16 and contact adhesive layer 17, suitable materials are as described above, e.g., polysiloxanes, polyisobutylenes, polyacrylates, polyurethanes, plasticized ethylene-vinyl acetate copolymers, low molecular weight polyether amide block polymers, tacky rubbers, and mixtures thereof.

Figure 3:
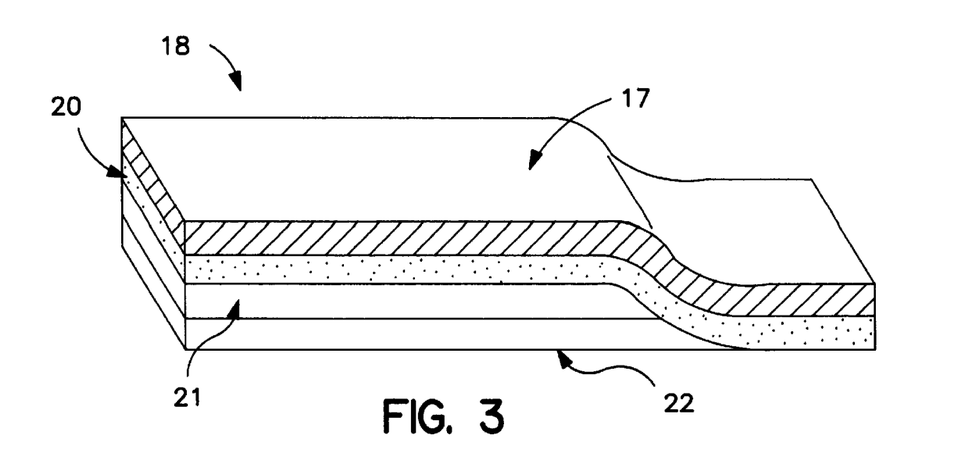
FIG. 3 illustrates in schematic form a liquid reservoir-type transdermal delivery system which may be used in conjunction with the present invention.
Figure 4:
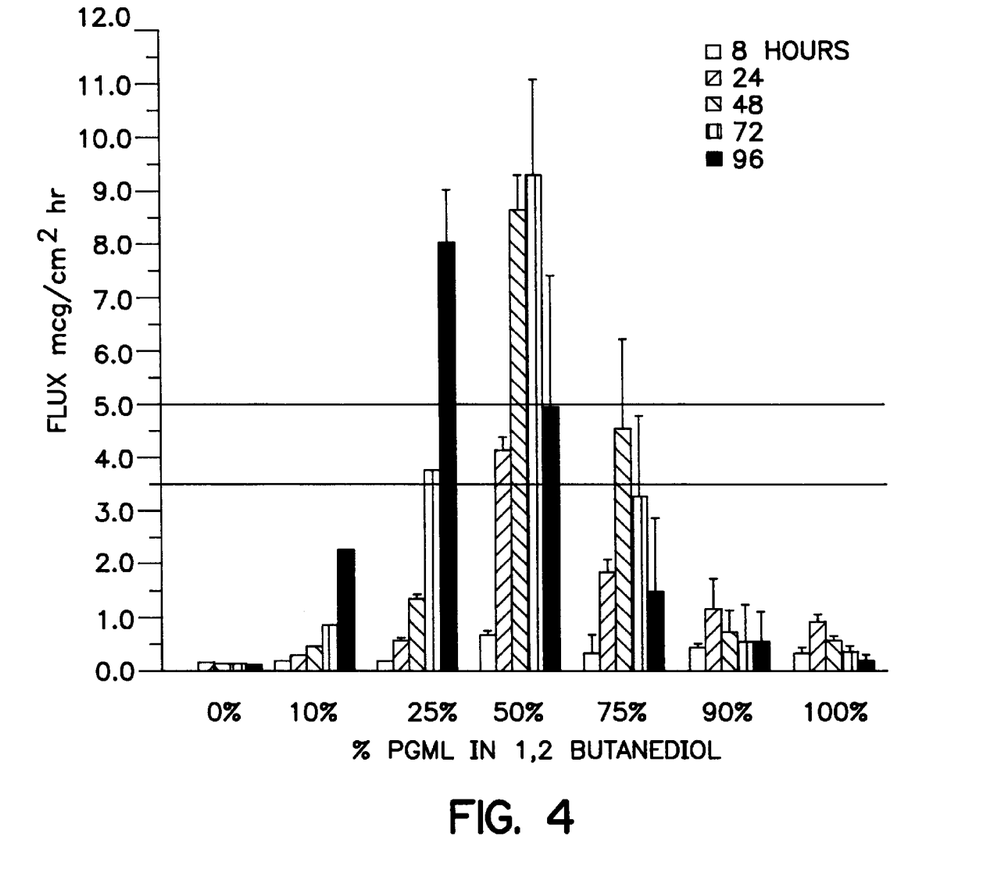
FIGS. 4–13 are graphs illustrating olanzapine flux obtained using various vehicles and prototypes, as described in the Examples herein.
Figure 5:
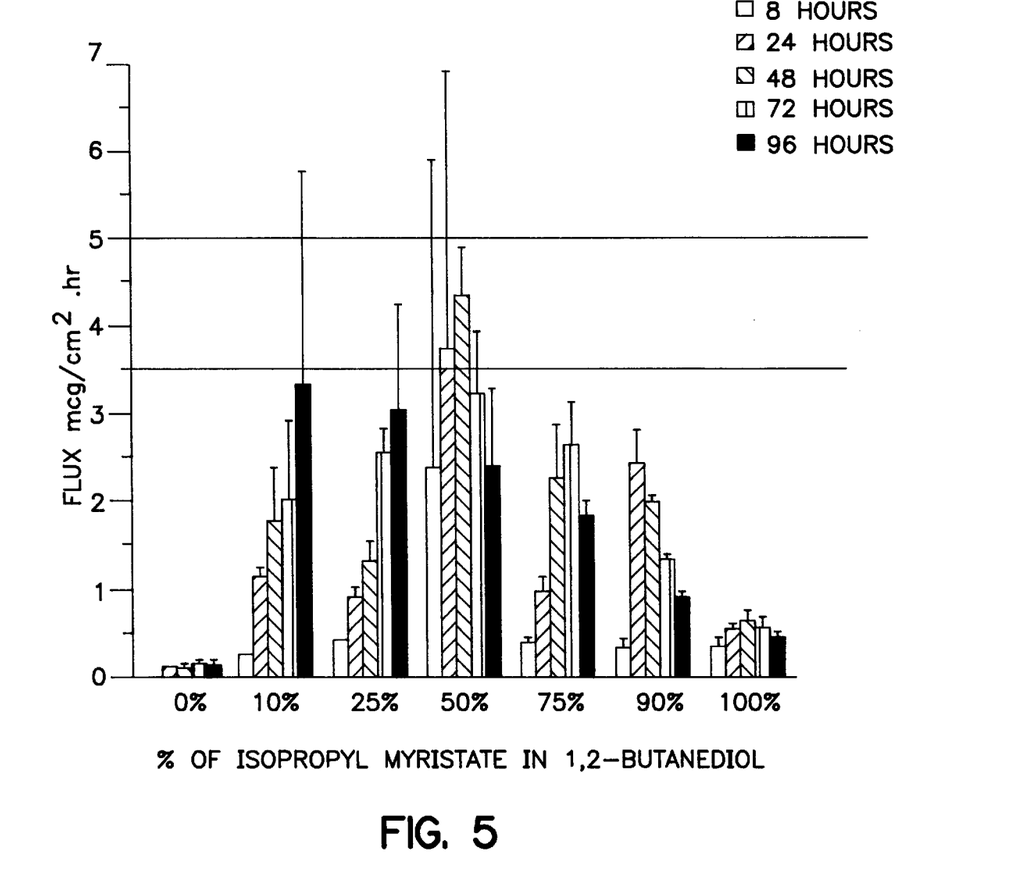
Figure 6:
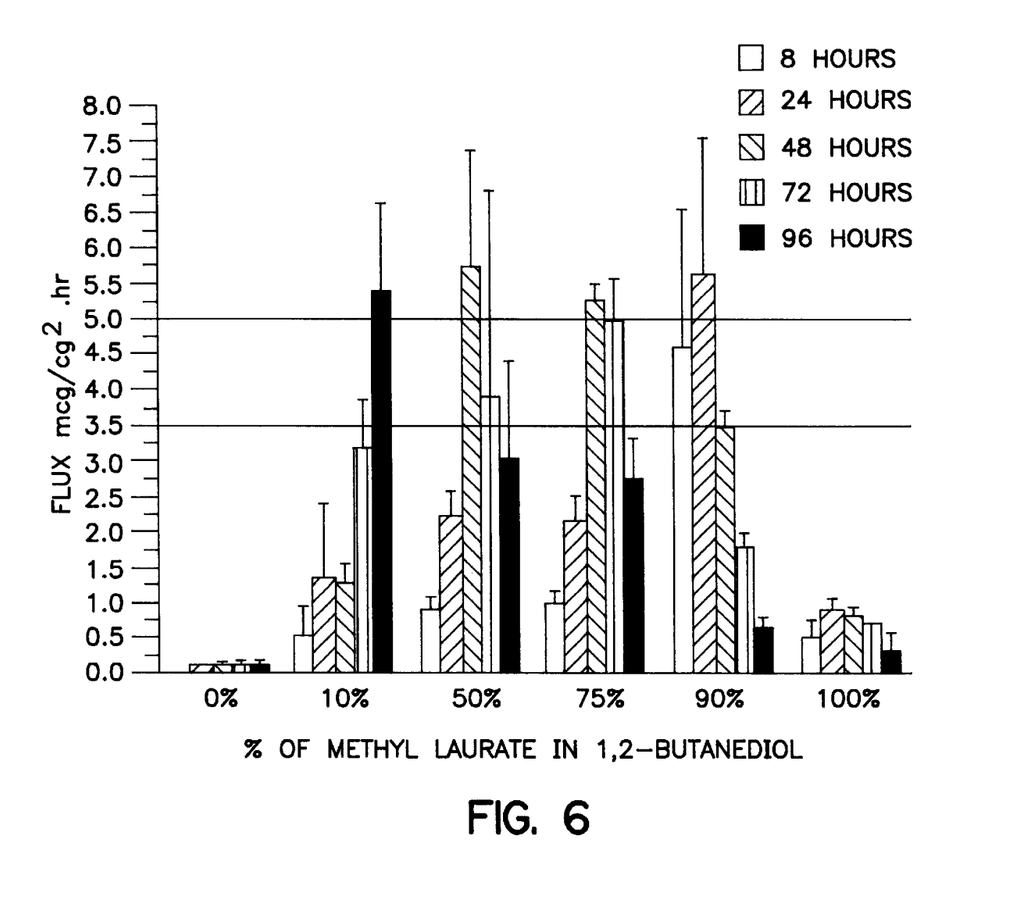
Figure 7:
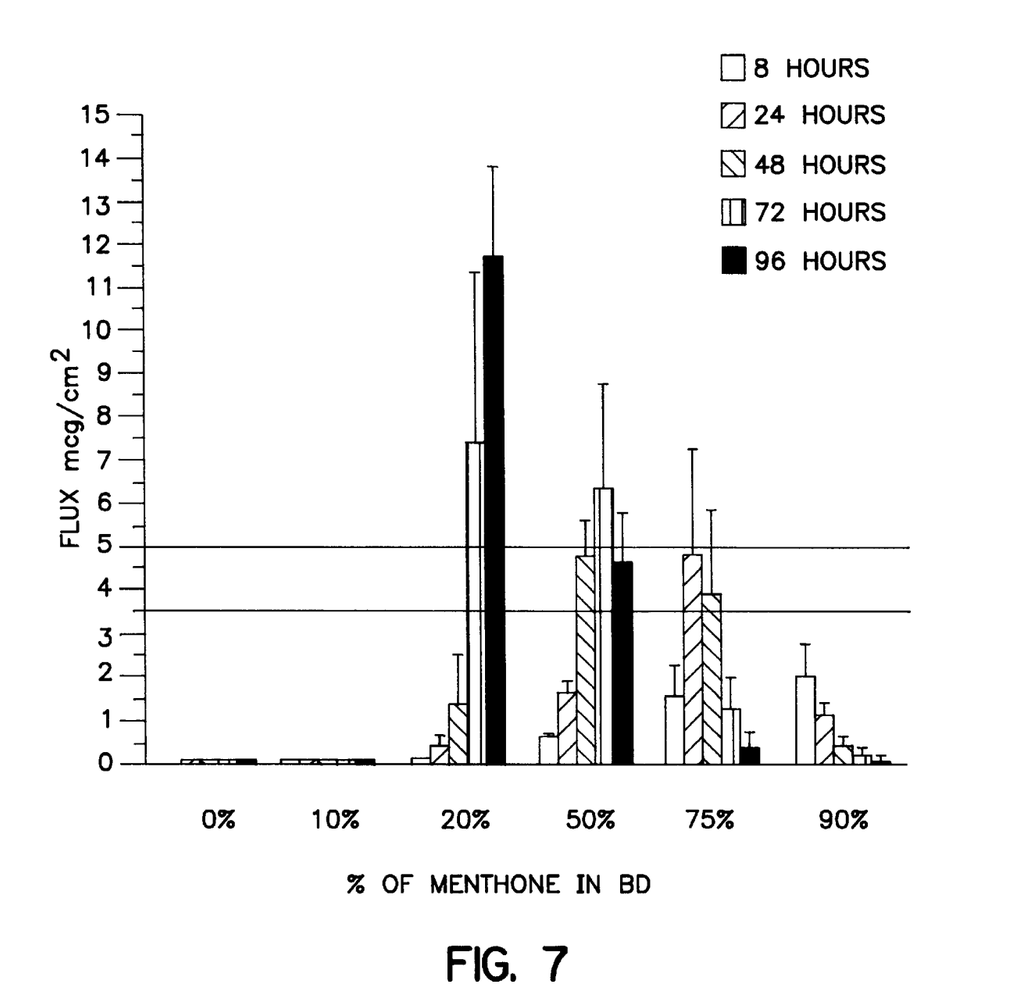
Figure 8:
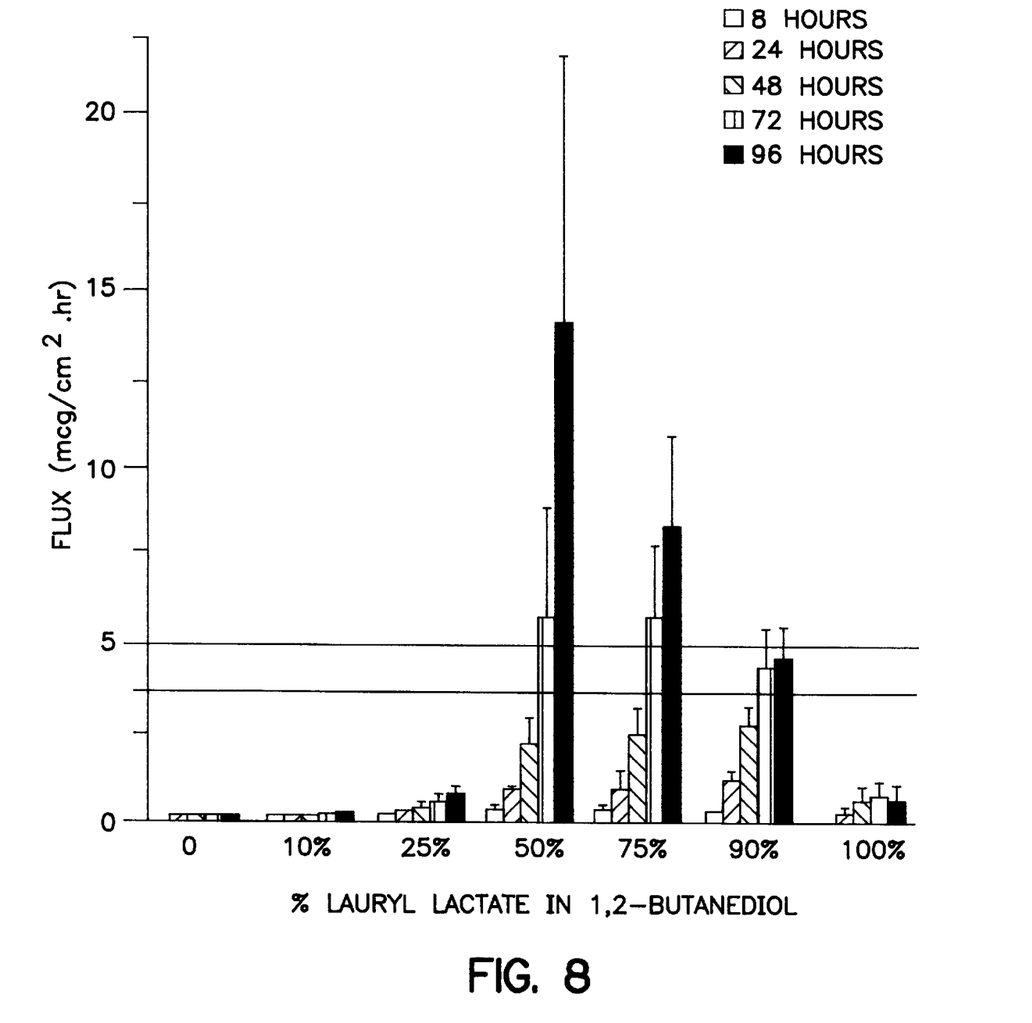

FIG. 3 depicts an alternative device structure for administering olanzapine or a salt thereof transdermally. The device is a "liquid reservoir" type and is generally designated 18. It comprises a top, impermeable backing layer 19, an underlying liquid, gel (e.g., a hydrogel as described below) or foam layer 20, generally a liquid layer, containing the drug and any associated materials, e.g., enhancers or the like, that is sealed at its edge to the overlying backing layer to form a pouch between the backing and the underlying modulator layer 21, and a pressure-sensitive adhesive layer 22 that serves as the basal surface of the device and affixes the device to the skin during use. The modulator layer is generally a thin, flexible layer of a highly porous material such as polyester, polyethylene, polypropylene, or the like. As with the above embodiments, the device of FIG. 3 is provided with a release liner (not shown) to protect adhesive layer 22 prior to use. Such devices are described, for example, in commonly assigned U.S. Pat. No. 5,124,157 to Colley et al.

Such transdermal drug delivery systems for use in conjunction with the administration of olanzapine or salts thereof can be fabricated using conventional techniques which are within the skill of the art, and/or explained in the literature. In general, devices of the invention are fabricated by solvent evaporation film casting, thin film lamination, die cutting, or the like.

Particularly preferred transdermal systems for administering olanzapine are those containing high capacity polyurethane hydrogel drug reservoirs, as described in commonly assigned U.S. patent application Ser. No. 08/528,105, entitled "TRANSDERMAL DRUG DELIVERY SYSTEMS HAVING POLYURETHANE HYDROGEL DRUG RESERVOIRS, AND ASSOCIATED METHODS OF MANUFACTURE AND USE," as well as those containing drug reservoirs fabricated from "superabsorbent" materials, such as described in commonly assigned U.S. patent application Ser. No. 08/528,655 entitled "TRANSDERMAL DRUG DELIVERY SYSTEMS HAVING SUPERABSORBENT DRUG RESERVOIRS, AND ASSOCIATED METHODS OF MANUFACTURE AND USE," now abandoned.

Briefly, transdermal systems containing high capacity, polyurethane hydrogel reservoirs are fabricated by crosslinking a polyurethane with a catalyst in the presence of water, or by photocuring in the presence of photoinitiator, in the presence of water. Drug formulation is incorporated into the hydrogel so formed, either during or after manufacture. As explained in the above-cited commonly assigned U.S. patent application, it is preferred that the hydrogel be fabricated such that the polyurethane starting material is crosslinked with an aliphatic, cycloaliphatic or aromatic diisocyanate in the presence of water, and that the drug formulation be absorbed therein following hydrogel formation. A laminated composite, containing the drug-containing hydrogel reservoir, a backing layer, optional additional layers such as a contact adhesive layer and a rate-controlling membrane, is then prepared, to serve as the delivery system to be affixed to the skin or mucosal tissue.

Drug reservoirs fabricated from superabsorbent materials are typically comprised of crosslinked polymers capable of absorbing at minimum 15 g drug formulation per g superabsorbent material (although polymers capable of absorbing far greater quantitites of drug formulation may be used as well). Examples of such superabsorbent materials, as explained in the above-identified patent application, are olefin/alkyl carboxylate copolymers, e.g., maleic anhydride-isobutylene copolymer, although other superabsorbent materials may also be used. As with the hydrogel-based system, a laminated composite may be prepared using conventional techniques, and serves as the transdermal drug delivery system.

In any of these transdermal systems, it may be desirable to include a rate-controlling membrane between the drug reservoir and a contact adhesive layer, when one is present. The materials used to form such a membrane are selected to limit the flux of non-drug components, i.e., enhancers, vehicles, and the like, from the drug reservoir, while not limiting the flux of drug. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like. A particularly preferred material useful to form the rate controlling membrane is ethylene-vinyl acetate copolymer.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

All patents, patent applications, and publications mentioned herein, both supra and infra, are hereby incorporated by reference.

Experimental

Materials and Methods

Olanzapine free base was provided by Eli Lilly. All chemicals were reagent grade.

In Vitro Skin Permeation of Olanzapine

Skin Preparation: Human cadaver skin was used for the permeation studies. The frozen skins were thawed and the epidermal layers (stratum corneum and viable epidermis) were separated from the full-thickness skin by immersing it in water at 60° C. for two min. This epidermis was either used immediately for flux studies or stored at −20° C. for later studies.

Skin permeation from vehicles: Modified Franz diffusion cells were used for evaluating the performance of vehicles for olanzapine delivery. The receiver compartment was filled with 7.5 ml of pH 7.4 buffer. Quantites ranging from 200 to 500 μl of the selected vehicles saturated with olanzapine were then placed into the donor compartment to initiate the skin flux experiments. The temperature of the diffusion cell contents was maintained at 32° C.±1° C. At predetermined times, the entire receiver content was withdrawn and replaced with fresh buffer. Samples were assays by HPLC.

Skin permeation from prototypes: Modified Franz cells were used for evaluating the prototype systems for delivery of olanzapine. The prototype systems were peeled off the polyester release liner and placed on top of the epidermis with the drug adhesive layer facing the stratum corneum. Gentle pressure was applied to insure full contact between the drug adhesive layer and the stratum corneum. The skin membrane with the olanzapine prototype system was then mounted carefully between the donor and the receiver compartments. The receiver compartment was filled with pH 7 buffer and the temperature was maintained at 32° C.±1° C. throughout the experimental period. The entire receiver content was withdrawn and replaced with fresh buffer. Samples were assayed by HPLC.

Flux determination: Skin flux ($\mu g/cm^2/hr$) was determined from the steady-state slope of the plot of the cumulative amount of olanzapine permeated through the skin versus time. After steady state had been established, the linear portion of the plot was used to calculate the flux from the slope. For some formulations, the steady state was not achieved, and the data were plotted as flux ($\mu g/cm^2/hr$) at each time point (dividing the quantity penetrating the skin during each time period, corrected for surface area by the time of penetration through the skin). Each formulation was run in triplicate, and the values reported represent the mean and standard deviation for three cells.

Skin Irritation Studies

The primary skin irritation potential of olanzapine formulations were determined. A Draize irritation protocol was used, as follows. The backs of six rabbits were clipped free of hair, and six different test materials were applied in small Hilltop chambers (0.2 ml) to the skin and worn for 24 hours. For the preliminary prototype, the system was applied to the rabbit skin, occluded using a release liner, and kept in place by means of an adhesive tape. The skin sites were scored according to the Draize scale at 24, 48 and 72 hours after application of the test materials. Mean primary irritation scores are as follows. Range of values: 0, non-irritating; 0–1.9, mildly irritating; 2–5.9, moderately irritating; and 6–8.0, severely irritating

EXAMPLE 1

Olanzapine was dissolved in a combination of two vehicles (as indicated in Table 1) and applied to human cadaver skin using a Franz diffusion cell. At predetermined time intervals, as shown in FIGS. 4–8, the whole receiver fluid was replaced with fresh fluid and analyzed for olanzapine using HPLC method. The formulations are listed in Table 1 and the flux data are illustrated in graph form in FIGS. 4–8.

TABLE 1

| Formulation | | |
|---|---|---|
| 1. | 90% | 1,2-butanediol + 10% PGML |
| 2. | 10% | 1,2-butanediol + 90% PGML |
| 3. | 25% | 1,2-butanediol + 75% PGML |

TABLE 1-continued

| Formulation | | |
|---|---|---|
| 4. | 75% | 1,2-butanediol + 25% PGML |
| 5. | 90% | 1,2-butanediol + 10% LL |
| 6. | 10% | 1,2-butanediol + 90% LL |
| 7. | 25% | 1,2-butanediol + 75% LL |
| 8. | 75% | 1,2-butanediol + 25% LL |
| 9. | 10% | 1,2-butanediol + 90% LL |
| 10. | 90% | 1,2-butanediol + 10% IPM |
| 11. | 25% | 1,2-butanediol + 75% IPM |
| 12. | 75% | 1,2-butanediol + 25% IPM |
| 13. | 100% | ML |
| 14. | 10% | 1,2-butanediol + 90% ML |
| 15. | 90% | 1,2-butanediol + 10% ML |
| 16. | 25% | 1,2-butanediol + 75% ML |
| 17. | 90% | 1,2-butanediol + 10% Menthone |
| 18. | 10% | 1,2-butanediol + 90% Menthone |
| 19. | 25% | 1,2-butanediol + 75% Menthone |
| 20. | 50% | 1,2-butanediol + 50% Menthone |

ML: Methyl Laurate, LL: Lauryl lactate, IPM: Isopropyl myristate.

EXAMPLE 2

Figure 9:
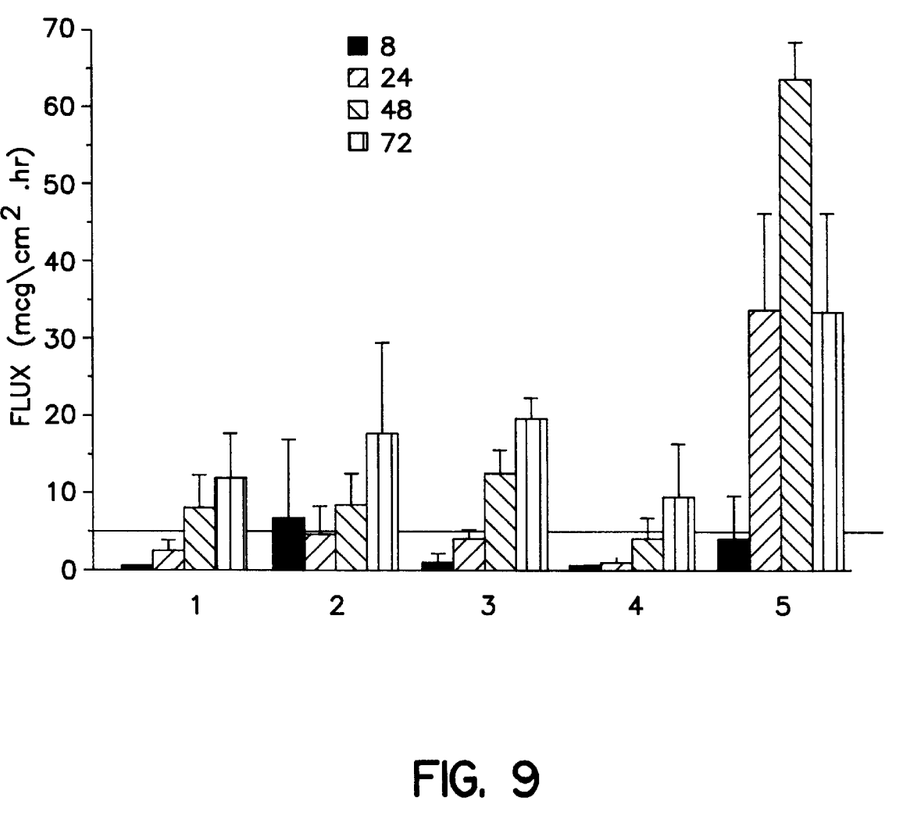

Olanzapine was dissolved in a combination of three vehicles (as indicated in Table 2). The procedure of Example 1 was followed to evaluate in vitro flux. The formulations are listed in Table 2 and the results are shown in FIG. 9.

TABLE 2

Formulation 1. 10% Oleic acid + 45% PGML + 45% 1,2-butanediol
2. 10% Oleyl alcohol + 45% PGML + 45% 1,2-butanediol
3. 10% Methyl laurate + 45% Lauryl lactate + 45% 1,2-butanediol
4. 10% Lauric acid + 45% PGML + 45% 1,2-butanediol
5. 10% Lauric acid + 45% Methyl Laurate + 45% 1,2-butanediol
6. 10% Capric acid + 45% Lauryl lactate + 45% 1,2-butanediol
7. 10% Benzyl alcohol + 45% PGML + 45% 1,2-butanediol
8. 10% Oleic acid + 45% Methyl decanoate + 45% 1,2-butanediol 110
9. 10% Capric acid + 90% Methyl Laurate ML: Methyl laurate; LL: Laurolactate; OA: Oleic acid; TG: Thioglycerol; PG: Propylene glycol

EXAMPLE 3

Figure 10:
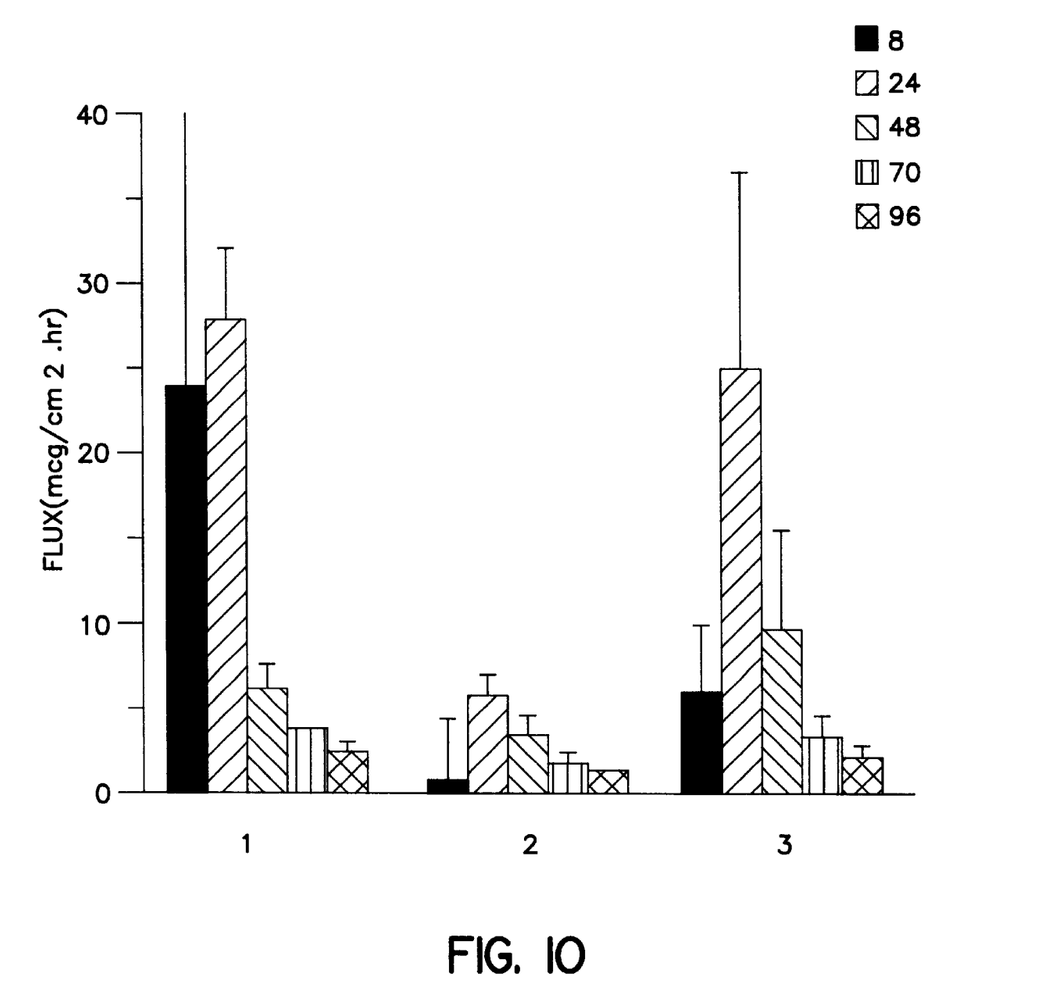

Olanzapine was dissolved in a combination of vehicles (as indicated in Table 3) and absorbed onto a highly absorbent maleic anhydride-isobutylene copolymeric film, obtained from Concert Industries Limited, Thurso, Quebec, Canada. The systems were cut into 1.25 $cm^2$ circles and applied onto the skin as in Example 1. The formulations are listed in Table 3 and the results are shown in FIG. 10.

TABLE 3

Formulation

1. Saturated olanzapine in vehicle of 10% lauric acid + 45% Methyl laurate + 45% 1,2-butanediol adsorbed on two pieces 1.25 $cm^2$ each of superabsorbent film (Concert 100136 #95068)
2. Saturated olanzapine in vehicle of 10% Oleyl alcohol + 45% PGML + 45% 1,2-butanediol adsorbed on two pieces 1.25 $cm^2$ each of superabsorbent film (Concert 100136 #95068)

TABLE 3-continued

| Formulation |
|---|
| 3. Saturated olanzapine in vehicle of 10% Oleic acid + 45% Methyl caprate + 45% 1,2-butanediol adsorbed on two pieces 1.25 cm² each of superabsorbent film (Concert 100136 #95068) |

EXAMPLE 4

Figure 11:
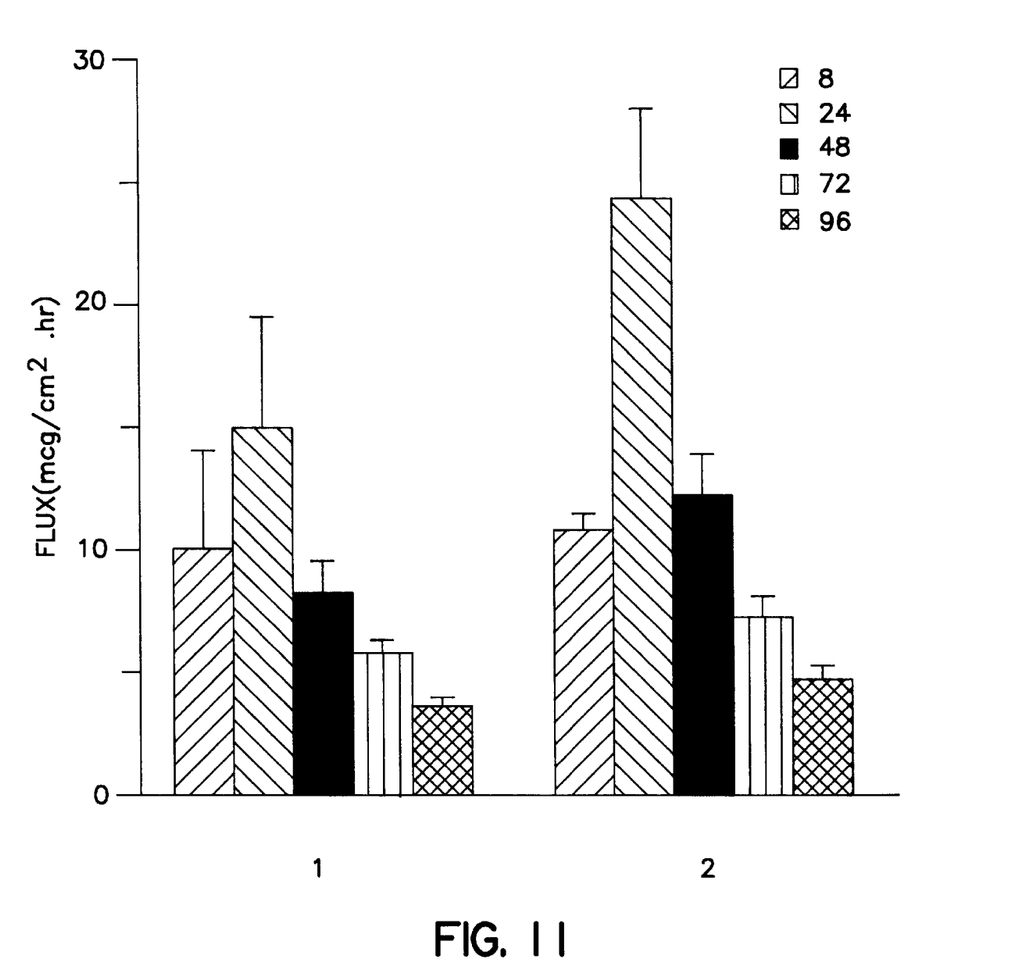

Olanzapine was dissolved in a combination of vehicles (see Table 4) and absorbed on a superabsorbent material as in Example 3. At the same time, a an ethylene vinyl acetate membrane was cut into 2 cm² circles and mounted onto the skin. Following this procedure, the polymeric film having drug absorbed thereon was applied and the procedure of Example 1 was followed. The formulations are listed in Table 4 and the results are shown in FIG. 11.

TABLE 4

| Formulation |
|---|
| 1. Olanzapine saturated in 10% Lauric acid + 45% methyl Laurate + 45% 1,2-butanediol and absorbed on superabsorbent film (Concert 100136 with EVA 19%, 4 mil membrane). |
| 2. Olanzapine saturated in 10% Oleic acid + 45% methyl caprate + 45% 1,2-butanediol and absorbed on superabsorbent film (Concert 100136 with EVA 19%, 4 mil membrane). |

EXAMPLE 5

Figure 12:
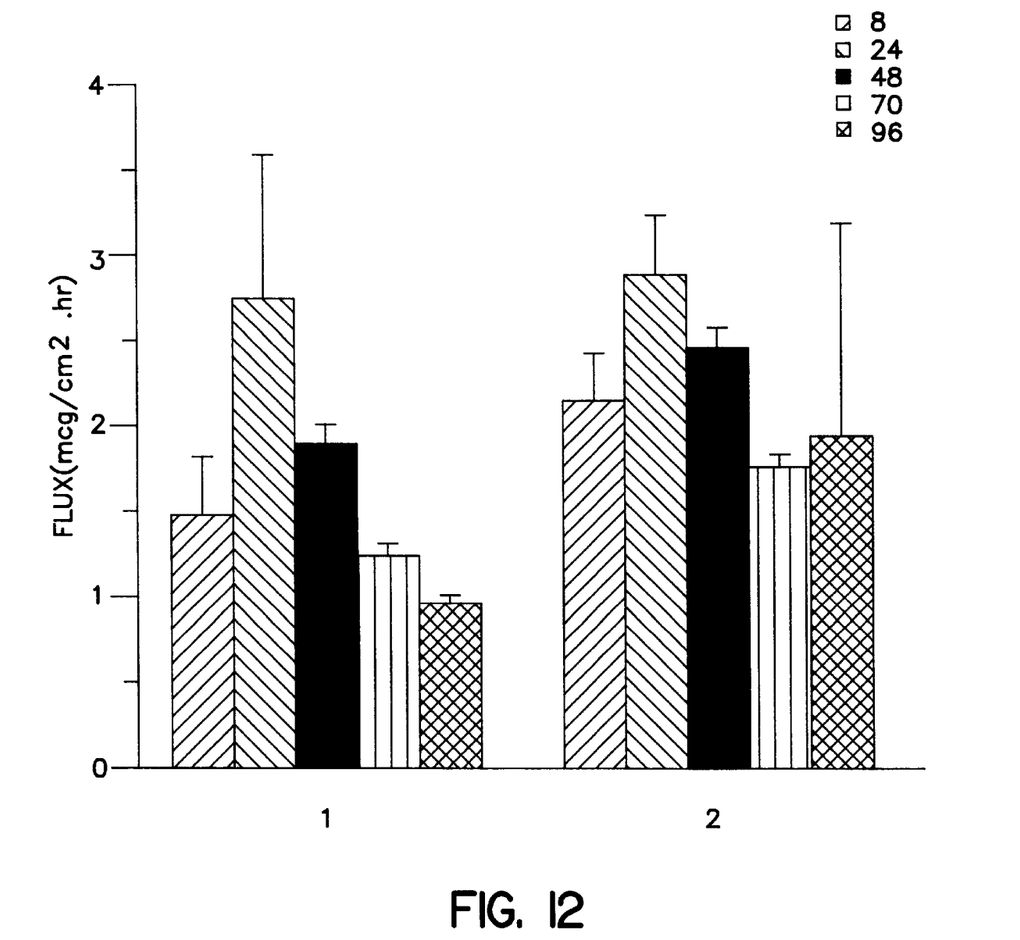

Olanzapine was dissolved in a combination of vehicles (see Table 5) and was added with water to Hypol® PreMA G-50 polymer (Hampshire Chemical Corporation) (ratio of water:polymer was approximately 2:1) and mixed together until a hydrogel was formed. The gel was cut into 2 cm² area circles and applied onto the skin as in Example 1. The formulations are listed in Table 5 and the results are shown in FIG. 12.

TABLE 5

| Formulation |
|---|
| 1. Hydrogel G-50 contains 25% Solution of saturated olanzapine in (10% Methyl Laurate + 45% Lauryl lactate + 45% 1,2-butanediol) |
| 2. Hydrogel G-50 contains 25% Solution of saturated olanzapine in (10% Lauric acid + 45% Lauryl lactate + 45% 1,2-butanediol) |

EXAMPLE 6

Figure 13:
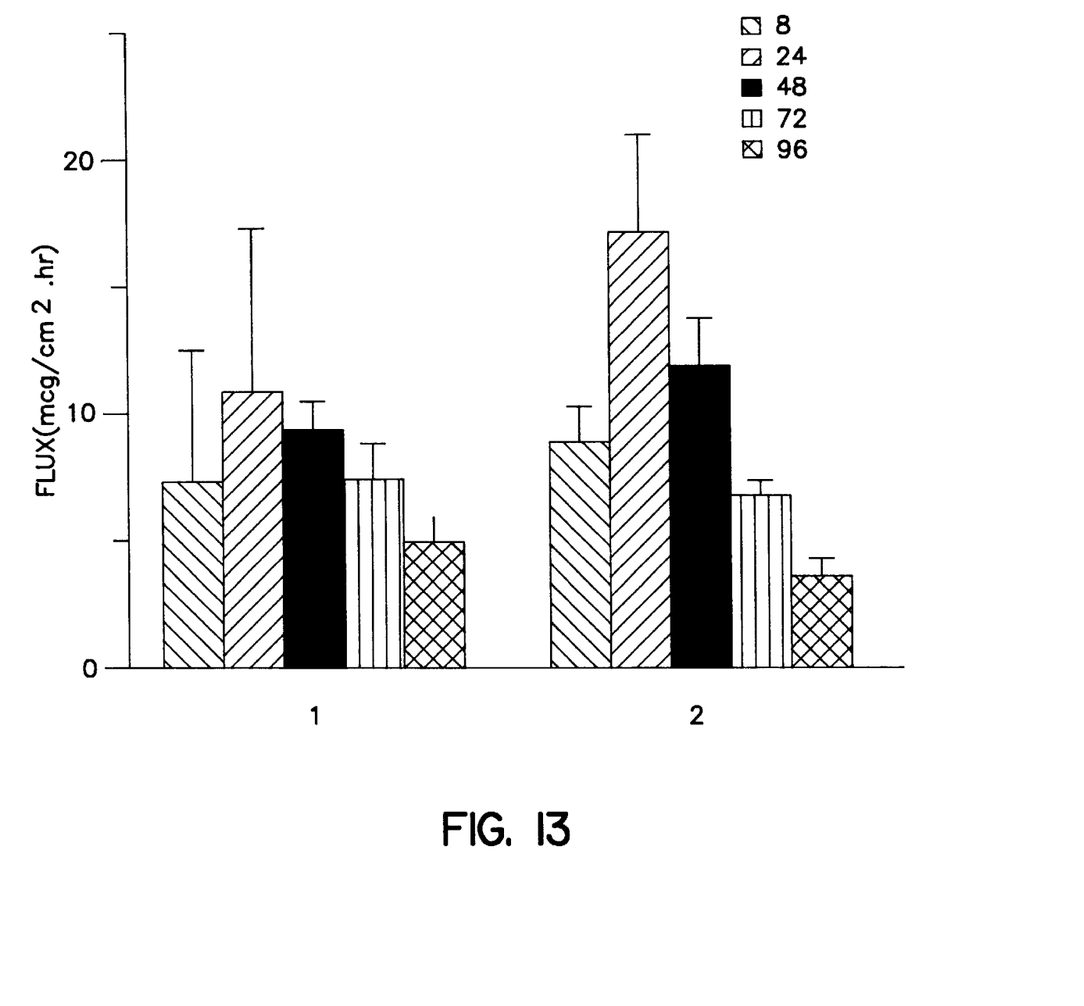

Olanzapine was dissolved in a combination of vehicles (as indicated in Table 6). Water was added to Hypol® PreMA G-50 polymer (Hampshire Chemical Corporation) (ratio of water:polymer was approximately 2:1) and mixed together until a hydrogel was formed. The gel was cut into 2 cm² circles which were then soaked with the olanzapine-vehicles combination overnight. The final product was applied onto the skin as in Example 1. The formulations are listed in Table 6 and the results are shown in FIG. 13.

TABLE 6

| Formulation |
|---|
| 1. Olanzapine saturated in 10% Lauric acid + 45% methyl Laurate + 45% 1,2-butanediol and left overnight with Hypol PreMA gel. |
| 2. Olanzapirie saturated in 10% Oieic acid + 45% methyl Caprate + 45% 1,2-butanediol and left overnight with Hypol PreMA gel. |

EXAMPLE 7

Results of the irritation studies conducted as explained above were as follows:

TABLE 7

Primary Irritation Score (Draize Score)

| Formulation | Draize Score |
|---|---|
| 1. Olanzapine saturated in PGML | 2.3 |
| 2. Olanzapine saturated in 10% Oleyl alcohol + 45% Methyl Caprate + 45% 1,2-butanediol and absorbed on the superabsorbent and a membrane (EVA 19%) was put in between the skin and the superabsorbent | 1.4 |
| 3. Olanzapine saturated in 10% Oleic acid + 45% Methyl Caprate + 45% 1,2-butanediol and absorbed on the superabsorbent and a membrane (EVA 19%) was put in between the skin and the superabsorbent | 1.4 |
| 4. Olanzapine saturated in 10% Lauric acid + 45% Methyl laurate + 45% 1,2-butanediol and absorbed on the superabsorbent and a membrane (EVA 19%) was put in between the skin and the superabsorbent | 1.4 |
| 5. Olanzapine saturated in 10% oleyl alcohol + 45% Methyl Caprate + 45% 1,2-butanediol in a Hypol PreMA G-50 Hydrogel | 1.7 |
| 6. Olanzapine saturated in 10% Lauric acid + 45% Methyl Laurate + 45% 1,2-butanediol in a Hypol PreMA G-50 Hydrogel | 2.2 |

As may be concluded from the results set forth in Table 7, irritation resulting from the formulations tested was minimal.

It may be concluded from these examples that sufficient skin fluxes of olanzapine can be achieved using any of a variety of enhancers, vehicles and prototypes, such that effective drug doses may be delivered using relatively small transdermal patches.

We claim:

1. A method for treating an individual suffering from or susceptible to psychosis, acute mania or anxiety, comprising applying a transdermal patch to intact skin or mucosal tissue of the individual and thereby transdermally administering a drug formulation comprising:

(a) at least one of olanzapine and pharmaceutically acceptable acid addition salts thereof; and
   (b) a skin permeation enhancer formulation comprising a $C_2$–$C_6$ alkanediol and at least one of: a fatty ester having the structural formula $[CH_3(CH_2)_m COO]_n R$, a fatty acid having the structural formula $CH_3(CH_2)_m COOH$, and a fatty alcohol having the structural formula $CH_3(CH_2)_m CH_2 OH$ wherein m is an integer in the range of 6 to 16, n is 1 or 2, and R is a lower alkyl ($C_1$–$C_3$) residue that is either unsubstituted or substituted with one or two hydroxyl groups.

2. The method of claim 1, wherein the individual is suffering from or susceptible to schizophrenia.

3. The method of claim 1, wherein the drug is olanzapine base.

4. The method of claim 1, wherein the drug is a pharmaceutically acceptable acid addition salt of olanzapine.

5. The method of claim 1, wherein the patch comprises a source of the drug and a means for maintaining the patch in drug transmitting relationship to the skin or mucosal tissue.

6. The method of claim 5, wherein the patch comprises a laminated composite of a backing layer that is substantially impermeable to the drug, and a reservoir layer having the drug dispersed therein.

7. The method of claim 6, wherein the reservoir layer is comprised of a pharmaceutically acceptable contact adhesive.

8. The method of claim 6, wherein the reservoir layer is comprised of a high capacity, polyurethane hydrogel.

9. The method of claim 6, wherein the reservoir layer is comprised of a superabsorbent, crosslinked polymeric material.

10. The method of claim 1 wherein the drug formulation is transdermally delivered from the patch such that the individual receives an effective daily dose over a three- to seven-day period.

11. A method for treating an individual suffering from or susceptible to psychosis, acute mania or anxiety, comprising applying a transdermal patch to intact skin or mucosal tissue of the individual and thereby transdermally administering a drug formulation comprising at least one of olanzapine and pharmaceutically acceptable acid addition salts thereof, wherein the transdermal patch includes a reservoir layer having the drug dispersed therein and wherein the reservoir is comprised of a high capacity, polyurethane hydrogel.

12. A method for treating an individual suffering from susceptible to psychosis, acute mania or anxiety, comprising applying a transdermal patch to intact skin or mucosal tissue of the individual and thereby transdermally administering a drug formulation comprising at least one of olanzapine and pharmaceutically acceptable acid addition salts thereof, wherein the transdermal patch includes a reservoir layer having the drug dispersed therein and wherein the reservoir is comprised of a superabsorbent, crosslinked polymeric material.

13. A transdermal patch for treating an individual suffering from or susceptible to psychosis, acute mania or mild anxiety, comprising a laminated composite of:

a reservoir layer having a drug formulation incorporated therein, wherein the drug formulation comprises
(a) at least one of olanzapine and pharmaceutically acceptable acid addition salts thereof, and
(b) a skin permeation enhancer formulation comprising a $C_2$–$C_6$ alkanediol and at least one of: a fatty ester having the structural formula $[CH_3(CH_2)_mCOO]_nR$, a fatty acid having the structural formula $CH_3(CH_2)_m COOH$, and a fatty alcohol having the structural formula $CH_3(CH_2)_mCH_2OH$ wherein m is an integer in the range of 6 to 16, n is 1 or 2, and R is a lower alkyl ($C_1$–$C_3$) residue that is either unsubstituted or substituted with one or two hydroxyl groups; and a backing layer that is substantially impermeable to the drug.

14. A transdermal patch for treating an individual suffering from or susceptible to psychosis, acute mania or mild anxiety, comprising a laminated composite of:

a reservoir layer having a drug formulation incorporated therein, wherein the drug formulation comprises at least one of olanzapine and pharmaceutically acceptable acid addition salts thereof, wherein the transdermal patch includes a reservoir layer having the drug dispersed therein and wherein the reservoir is comprised of a high capacity, polyurethane hydrogel; and a backing layer that is substantially impermeable to the drug.

15. A transdermal patch for treating an individual suffering from or susceptible to psychosis, acute mania or mild anxiety, comprising a laminated composite of:

a reservoir layer having a drug formulation incorporated therein, wherein the drug formulation comprises at least one of olanzapine and pharmaceutically acceptable acid addition salts thereof, wherein the transdermal patch includes a reservoir layer having the drug dispersed therein and wherein the reservoir is comprised of a superabsorbent, crosslinked polymeric material; and a backing layer that is substantially impermeable to the drug.

16. A pharmaceutical formulation comprising a drug selected from the group consisting of olanzapine and pharmaceutically acceptable acid addition salts thereof, and a skin permeation enhancer formulation comprising a $C_2$–$C_6$ alkanediol and at least one of: a fatty ester having the structural formula $[CH_3(CH_2)_mCOO]_nR$, a fatty acid having the structural formula $CH_3(CH_2)_mCOOH$, and a fatty alcohol having the structural formula $CH_3(CH_2)_mCH_2OH$ wherein m is an integer in the range of 6 to 16, n is 1 or 2, and R is a lower alkyl ($C_1$–$C_3$) residue that is either unsubstituted or substituted with one or two hydroxyl groups.

17. The formulation of claim 16, wherein the drug is olanzapine base.

18. The formulation of claim 16, wherein the drug is a pharmaceutically acceptable olanzapine salt.

19. The transdermal patch of claim 13, wherein the reservoir layer is comprised of a pharmaceutically acceptable contact adhesive.

20. The transdermal patch of claim 13, wherein the reservoir layer is comprised of a high capacity, polyurethane hydrogel.

21. The transdermal patch of claim 13, wherein the reservoir layer is comprised of a superabsorbent crosslinked polymeric material.

22. The transdermal patch of claim 13, wherein the drug is olanzapine base.

23. The transdermal patch of claim 13, wherein the drug is a pharmaceutically acceptable olanzapine salt.

* * * * *